(12) United States Patent
Biedermann et al.

(10) Patent No.: US 9,277,941 B2
(45) Date of Patent: Mar. 8, 2016

(54) BONE ANCHORING DEVICE

(75) Inventors: Lutz Biedermann, VS-Villingen (DE); Wilfried Matthis, Weisweil (DE); Berthold Dannecker, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 250 days.

(21) Appl. No.: 13/314,085

(22) Filed: Dec. 7, 2011

(65) Prior Publication Data
US 2012/0172932 A1 Jul. 5, 2012

Related U.S. Application Data

(60) Provisional application No. 61/421,978, filed on Dec. 10, 2010.

(30) Foreign Application Priority Data

Dec. 10, 2010 (EP) .................................... 10194601

(51) Int. Cl.
*A61B 17/70* (2006.01)

(52) U.S. Cl.
CPC .................................. *A61B 17/7037* (2013.01)

(58) Field of Classification Search
CPC .................................................. A61B 17/7037
USPC ......... 606/300–303, 319, 320, 322, 326–328, 606/264–270, 272
See application file for complete search history.

(56) References Cited

U.S. PATENT DOCUMENTS

| 6,010,503 | A  | * | 1/2000 | Richelsoph et al. | .......... 606/278 |
| 7,699,876 | B2 | * | 4/2010 | Barry et al. | ................... 606/266 |
| 8,002,806 | B2 | * | 8/2011 | Justis | ............................ 606/264 |
| 2006/0129149 | A1 | * | 6/2006 | Iott et al. | ........................ 606/61 |
| 2008/0015576 | A1 | * | 1/2008 | Whipple | ........................ 606/60 |

(Continued)

FOREIGN PATENT DOCUMENTS

| CN | 101828949 A | 9/2010 |
| EP | 2 022 423 A1 | 2/2009 |

(Continued)

OTHER PUBLICATIONS

European Search Report for European Application No. EP 10 19 4601, European Search Report dated Mar. 24, 2011 and mailed Apr. 5, 2011 (5 pgs.).

*Primary Examiner* — Jan Christopher Merene
*Assistant Examiner* — Atiya Mahmud
(74) *Attorney, Agent, or Firm* — Lewis Roca Rothgerber Christie LLP (57) ABSTRACT

A bone anchoring device includes a bone anchoring element including a shaft and a head, a receiving part for coupling a rod to the bone anchoring element, the receiving part including a rod receiving portion having a channel with a bottom for receiving a rod, and a head receiving portion to allow introduction and clamping of the head, and a locking ring including at least one projection, wherein the rod receiving portion has at least one cutout, wherein when the head is not locked, the projection is configured to extend through the cutout and into the channel, and wherein a first engagement portion is provided on the locking ring for engaging a second engagement portion at an inner wall of the cutout to hold the locking ring in a first position where the head is pivotable in the head receiving portion but is prevented from removal therefrom.

22 Claims, 5 Drawing Sheets

(56) References Cited

U.S. PATENT DOCUMENTS

| | | | |
|---|---|---|---|
| 2008/0161859 A1* | 7/2008 | Nilsson | 606/266 |
| 2008/0269742 A1* | 10/2008 | Levy et al. | 606/60 |
| 2009/0036934 A1* | 2/2009 | Biedermann et al. | 606/301 |
| 2009/0149887 A1* | 6/2009 | Schlaepfer et al. | 606/278 |
| 2009/0204155 A1* | 8/2009 | Aschmann | 606/264 |
| 2010/0063552 A1* | 3/2010 | Chin et al. | 606/302 |
| 2010/0160976 A1 | 6/2010 | Biedermann et al. | |
| 2010/0168801 A1* | 7/2010 | Biedermann et al. | 606/302 |
| 2011/0160778 A1* | 6/2011 | Elsbury | 606/305 |

FOREIGN PATENT DOCUMENTS

| | | |
|---|---|---|
| EP | 2 201 903 A1 | 6/2010 |
| WO | WO 2007/038350 A2 | 4/2007 |

\* cited by examiner

BONE ANCHORING DEVICE

CROSS-REFERENCE TO RELATED APPLICATION(S)

The present application claims the benefit of U.S. Provisional Patent Application Ser. No. 61/421,978, filed Dec. 10, 2010, the contents of which are hereby incorporated by reference in their entirety, and claims priority from European Patent Application EP 10 194 601.0, filed Dec. 10, 2010, the contents of which are hereby incorporated by reference in their entirety.

BACKGROUND

1. Field of the Invention

The invention relates to a bone anchoring device including a bone anchoring element and a receiving part for connecting the bone anchoring element to a rod. The head of the bone anchoring element is locked in the receiving part by compression of a portion of the receiving part laterally surrounding the head by means of a locking ring, which is pressed down by the rod. The locking ring has two upwardly extending projections that extend into the channel for the rod and can be engaged by the rod to exert pressure onto the locking ring. The upwardly extending projections cooperate with the receiving part in such a way that the locking ring can assume a position in which the head is pivotable in the head receiving portion but can not be removed from the head receiving portion.

2. Description of Related Art

A bone anchoring device which includes a bone anchoring element and a receiving part with a rod receiving portion and a head receiving portion and a locking ring for locking the head in the head receiving portion is known from EP 2 022 423 A1. Below the bottom of the channel for the rod in the rod receiving portion cutouts are provided on either end of the channel, through which two upwardly extending projections of the locking ring extend into the channel, so that they are engageable by the rod. In one embodiment, the upwardly extending projections have lateral projections which snap into the channel to prevent the locking ring from falling off when the head is not inserted into the head receiving portion.

WO 2007/038350 A2 describes an apparatus for connecting a bone anchor to a support rod, the apparatus including a connector body and a cap. The connector body has a channel to receive and locate the support rod relative to the bone anchor. A sleeve fits over a socket portion of the connector body in a temporary position, in which the sleeve permits insertion of the bone anchor into the socket. The sleeve can then be moved to a provisional locking position, in which the sleeve permits angulation but prevents removal of the bone anchor and can further be moved to a locking position in which the sleeve prevents both angulation and removal of the bone anchor.

SUMMARY

It is an object of the invention to provide an improved bone anchoring device which has a small size and which allows for safe handling during surgery.

In an embodiment of the invention, the bone anchoring device provides a pre-locking position for a. locking ring, in which a head of a bone anchoring element (e.g., a screw element) can be pivoted but cannot be removed from a head receiving portion of a receiving part. The pre-locking position is achieved by an engagement of the locking ring with the receiving part in a region corresponding to rod supporting projections, which extend into a channel for a rod. This allows for simplifying of the design of the locking ring in an area which clamps the head. Also, an overall size of the bone anchoring device, in particular with respect to a largest outer diameter of the bone anchoring device, can be decreased. Therefore, the bone anchoring device may be particularly suitable for applications in the cervical spine.

The pre-locking position of the locking ring provides for safe handling during surgery, since the head of the bone anchoring element cannot be removed from the receiving part inadvertently.

BRIEF DESCRIPTION OF THE DRAWINGS

Further features and advantages of the invention will become apparent from the description of embodiments by means of the accompanying drawings. In the drawings:

FIG. 3b shows an enlarged portion of FIG. 3a;

FIG. 8b shows an enlarged portion of FIG. 8a;

FIG. 9b shows an enlarged portion of FIG. 9a;

FIG. 10a shows a side view of the bone anchoring device of FIG. 1, with the head of the bone anchoring element introduced into the receiving part and the locking ring in a second position;

FIG. 10b shows an enlarged portion of FIG. 10a;

FIG. 11b shows an enlarged portion of FIG. 11a.

DETAILED DESCRIPTION

As shown in FIGS. 1 to 3b, the bone anchoring device according to one embodiment includes a bone anchoring element 1 in the form of a bone screw having a threaded shaft 2 and a spherical segment-shaped head 3. The head 3 has a recess 4 for engagement with a driver or tool. The bone anchoring device further includes a receiving part 5 for receiving a rod 6 to connect the rod 6 to the bone anchoring element 1. Further, a closure element 7 in the form of an inner screw or set screw is provided for securing the rod 6 in the receiving part 5. In addition, the bone anchoring device includes a locking ring 8 for locking the head 3 in the receiving part 5.

The receiving part 5 includes a rod receiving portion 9, which has a first end 9a and an opposite second end 9b. The rod-receiving portion 9 is substantially cylindrical and has a coaxial first bore 10 provided at the second end 9b. The diameter of the first bore 10 is smaller than the diameter of the head 3 of the bone anchoring element 1. Therefore, the head 3 cannot extend into the rod receiving portion 9. The rod receiving portion 9 also has a coaxial second bore 11 extending from the first end 9a to a distance from the second end 9b. The diameter of the second bore 11 is larger than that of the first bore 10 and larger than the diameter of the rod 6. A U-shaped recess 12 is provided in the rod receiving portion 9, which extends from the first end 9a towards the second end 9b. The U-shaped recess 12 forms a channel for the rod 6, and is sized such that the rod 6 can be placed and guided therein. By means of the U-shaped recess 12 two free legs 12a, 12b are formed, on which an internal thread 13 is provided. The internal thread can be a metric thread, a flat thread, a negative angle thread, a saw-tooth thread or any other thread. Preferably, a thread form such as a flat thread or a negative angle thread is used, for preventing splaying of the legs 12a, 12b when the inner screw 7 is screwed into the receiving part. The depth of the U-shaped recess 12 is such that the rod 6 and the inner screw 7 can be inserted between the legs 12a, 12b. Near the bottom of the recess 12, a substantially flat section 14 is provided forming an end of the bore 11.

The rod receiving portion 9 of the receiving part 5 has a plurality of coaxial slits 15 extending from the second end 9b to a distance from the first end 9a, the distance corresponding approximately to the length of the internal thread 13. The slits are open at the second end 9b and extend through the substantially flat section 14, as can be seen for example in FIG. 3a. The number of slits is provided according to the desired degree of elasticity to facilitate introduction of the head 3 into the receiving part 5. Other factors may include, for example, the material and the wail thickness and/or other factors.

As can be seen in particular in FIGS. 1 and 7 to 9b, the rod receiving portion 9 has cutouts 24, which extend from the second end 9b to the bottom of the U-shaped recess 12. The cutouts 24 are provided at either end of the U-shaped recess 12 in a direction along an axis of the channel. At a transition between the cutouts 24 and the vertical wall 5 of the U-shaped recess 12, inwardly extending noses 25 are formed, each nose having a vertical inner wall portion 25a and perpendicular thereto a horizontal lower wall portion 25b. The noses 25 are provided on either side of the channel formed by the U-shaped recess so that each cutout 24 is provided with two noses 25, respectively. As such, the width of the cutouts 24 at the noses 25 is reduced.

Adjacent to the second end 9b, the receiving part 5 includes a head receiving portion 16 providing an accommodation space for the head 3 of the bone anchoring element 1. The head receiving portion 16 has a free end 17 opposite to the second end 9b of the rod receiving portion 9. As can be seen in particular in FIG. 3a, a maximum outer diameter of the head receiving portion 16 is smaller than an outer diameter of the rod receiving portion 9, so that the head receiving portion 16 is recessed with respect to the rod receiving portion 9. The head receiving portion 16 has an internal hollow section 18, which in the embodiment shown is spherically-shaped with a radius matching or corresponding to a radius of the head 3 of the bone anchoring element 1. The internal hollow section 18 has an opening 19 at the free end 17. The dimensions of the internal hollow section 18 are such that the hollow section 18 encompasses the head 3 of the bone anchoring element including a region corresponding to a largest diameter of the head 3.

Figures 1, 2:
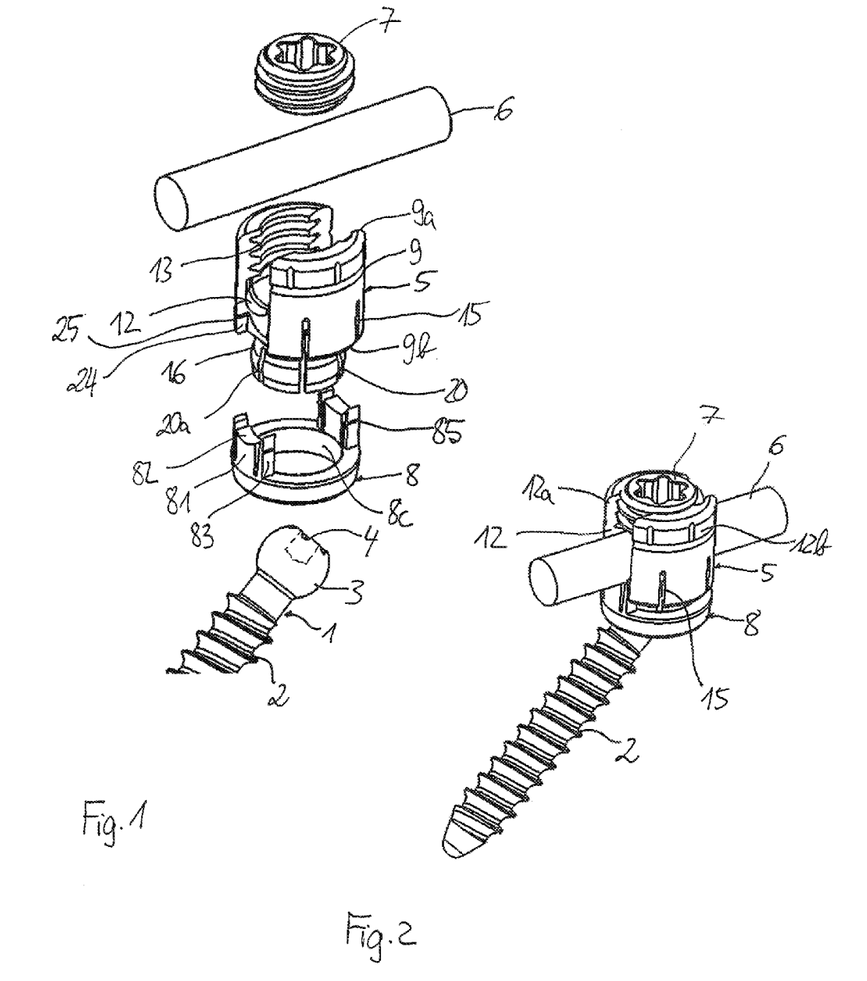
FIG. 1 shows a perspective exploded view of an embodiment of the bone anchoring device.
FIG. 2 shows a perspective view of the bone anchoring device of FIG. 1 in an assembled state.

As can be seen in particular in FIG. 1, slits 20 are provided in the head receiving portion 16, the slits 20 being open to the free end 17, and which may continue into the slits 15 of the rod receiving portion 9. There may also be one or more slits 20a, which end in the head receiving portion at a position above the largest diameter of the head (i.e., the slits 20a do not continue into the rod receiving portion 9). For example, at positions corresponding to the U-shaped recess 12, slits 20a may be provided. The slits 20 and/or 20a in the head receiving portion 16 render the head receiving portion 16 flexible, such that the head 3 of the bone anchoring element 1 can be inserted by expanding the head receiving portion 16, and can be clamped in the head receiving portion 16 by compression of the head receiving portion 16.

An outer surface of the head receiving portion 16 includes an outwardly curved section 16a, which serves for cooperation with the locking ring 8, as described below.

Figure 4:
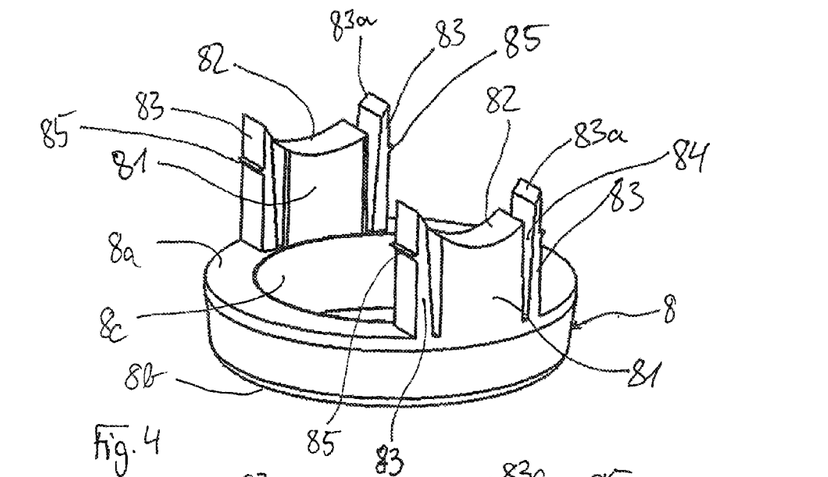
FIG. 4 shows a perspective view of a locking ring of a bone anchoring device according to one embodiment.
Figures 5, 6:
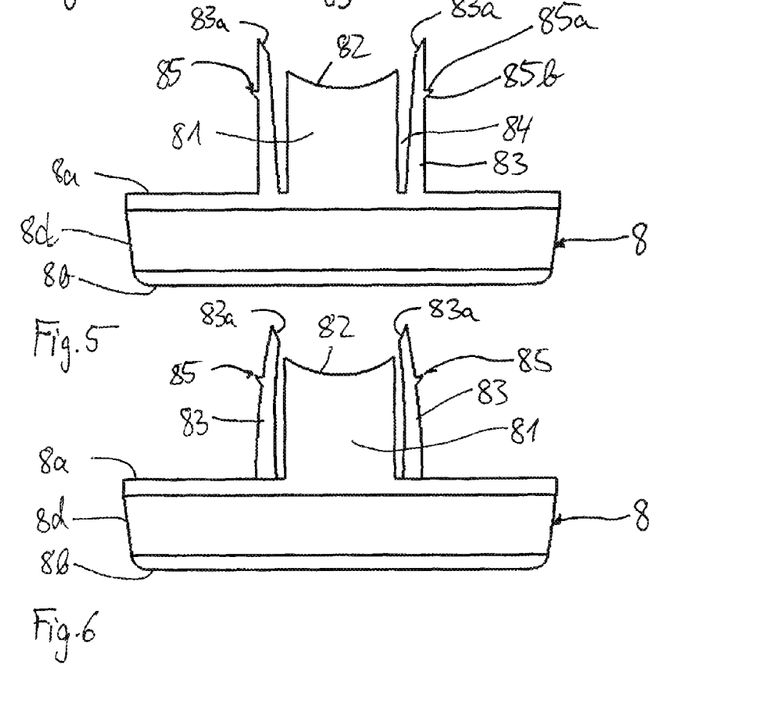
FIG. 5 shows a side view of the locking ring of FIG. 4 in a first condition.
FIG. 6 shows a side view of the locking ring of FIG. 4 in a second condition.

The locking ring 8 will now be described with reference to FIGS. 4 to 6. The locking ring 8 has an upper end 8a facing the second end 9b of the rod receiving portion 9 of the receiving part 5 in a mounted state, and a lower end 8b. The inner wall of the locking ring, has a portion 8c that is substantially cylindrical. The portion 8c may extend from the upper end 8a to the lower end 8b, but is at least provided in a region positioned to cooperate with the curved outer surface portion 16a of the head receiving portion 16. An inner diameter of the cylindrical portion 8c of the locking ring 8 is slightly smaller than an outer diameter of the curved portion 16a of the head receiving portion 16 in a resting position, to allow compression of the head receiving portion 16 by the locking ring 8. The flexibility of the head receiving portion 16 allows mounting of the locking ring 8 from the free end 17 onto the head receiving portion 16 by slightly compressing the head receiving portion 16. The locking ring 8 further has a substantially conical or cylindrical outer surface 8d with a maximum outer diameter that is the same or smaller than the outer diameter of the rod receiving portion 9, so that, as shown in FIG. 2, when the locking ring 8 is mounted on the receiving part 5, the locking ring 8 does not extend radially outwards from the receiving part 5. This provides for a compact shape of the bone anchoring device.

Figure 3A:
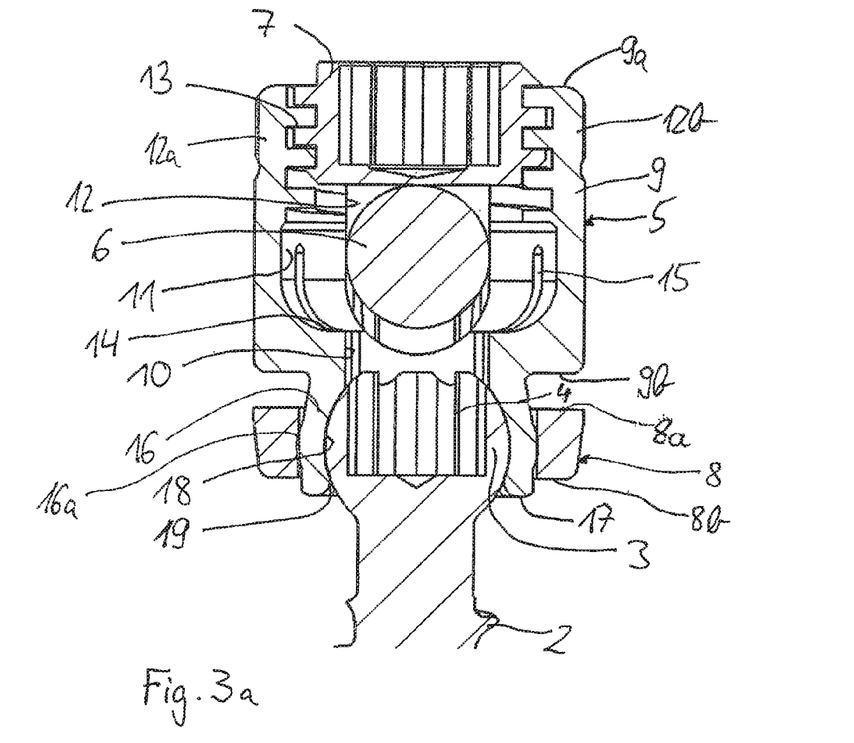
FIG. 3a shows a cross-sectional view of the bone anchoring device of FIG. 2, the section being taken perpendicular to a rod axis.
Figure 3B:
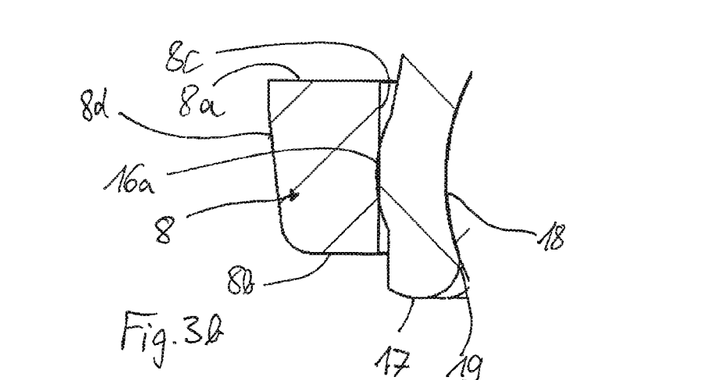

The height of the locking ring 8 in an axial direction (Le, from upper end 8a to lower end 8b) is smaller than that of the head receiving portion 16 of the receiving part 5 so that, as shown in FIG. 3a, there may be a distance between the upper end 8a of the locking ring 8 and the second end 9h of the rod receiving portion 9, when the locking ring 8 is in a position around the head receiving portion 16.

The locking ring 8 further comprises at its upper end 8a two projections 81 located diametrically opposite to each other. The projections 81 have such a height that they extend into the cutouts 24 and project above the bottom of the U-shaped recess 12 when the locking ring 8 is in a position in which the head 3 is not locked. A free end 82 of the projections 81 can be curved with a curvature corresponding to a curvature of the rod 6.

At either side of each projection 81, an upwardly extending spring portion 83 is provided. The spring portions 83 are flexible in such a way that they can be elastically bent towards the projections 81. A cross-section of the spring portions 83 may be substantially trapezoidal, with thickness decreasing towards free ends 83a. The free ends 83a can be adapted to the shape of the rod 6, so that the rod 6, when it is introduced into the U-shaped recess 12, rests on the upper surface 82 of the projections 81 and on the free end 83*a* of the spring portions 83. The flexibility of the spring portions 83 depend on the thickness of the spring portions 83 in a circumferential direction and on a size of gaps 84 between the projection 81 and the spring portions 83, among other factors. Each spring portion 83 includes, at a distance from the upper end 8*a*, a horizontally outward extending projection 85 with a horizontal upper side 85*a* and an inclined lower side 85*b*. The horizontally extending projections 85 are positioned at such a height that when they cooperate with the noses 25 as explained below, the upper surface 82 of the projections 81 extend into the U-shaped recess 12.

Figure 7:
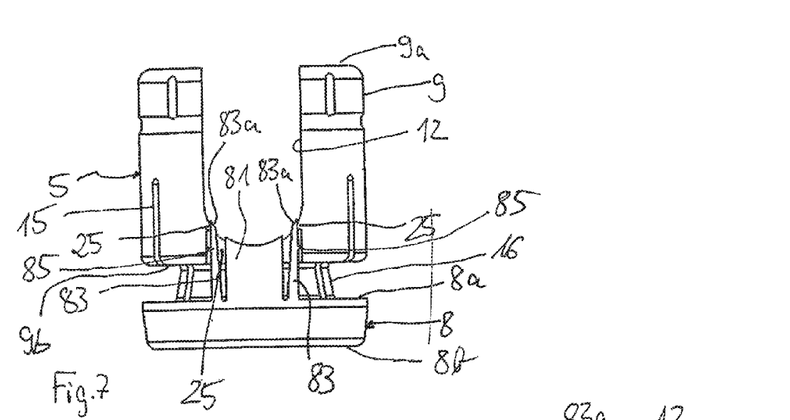
FIG. 7 shows a side view of a receiving part and the locking ring of FIG. 1, wherein the locking ring is mounted from the bottom end of the receiving part.
Figure 8A:
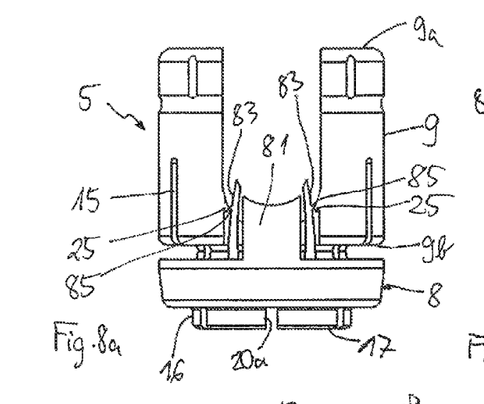
FIG. 8a shows a side view of the receiving part with mounted locking ring of FIG. 1 during a step of entering a first position of the locking ring.

When the upwardly extending spring portions 83 are not deflected, they may extend through the cutouts 24 as shown in FIG. 7. A distance between the outermost edges of the horizontally extending projections 85 is larger than a distance between the vertical inner walls 25*a* of the two noses 25 as also shown in FIG. 7. By deflecting the spring portions 83, the distance between the outer edges of the horizontally extending projections 85 is decreased, as shown in FIG. 8*a*.

The inner screw 7 has a thread cooperating with the internal thread 13 provided on the legs 12*a*, 12*b*. If a thread form which prevents the legs from splaying is used, a single closure element such as the inner screw 7 is sufficient. This reduces the size of the bone anchoring device in a radial direction.

The receiving part 5, the locking ring 8, the inner screw 7, and the bone anchoring element 1 may be made of a biocompatible material, for example, of titanium or stainless steel, or of a bio-compatible alloy, such as Nitinol, or of a bio-compatible plastic material such as, for example, polyether-etherketone (PEEK). The parts may be made of or include the same material or different materials.

Steps for mounting the locking ring 8 onto the receiving part 5 will be described with reference to FIGS. 7 to 9*b*. In a first step, as shown in FIG. 7, the locking ring 8 is mounted from the free end 17 of the head receiving portion 16, such that the projections 81 are aligned with the U-shaped recess 12. The projections 81 and the upwardly extending spring portions 83 are introduced into the cutouts 24 until the upper edges 83*a* are above the noses 25. The horizontally extending projections 85 are still within the cutouts 24 at this point.

Figure 8B:
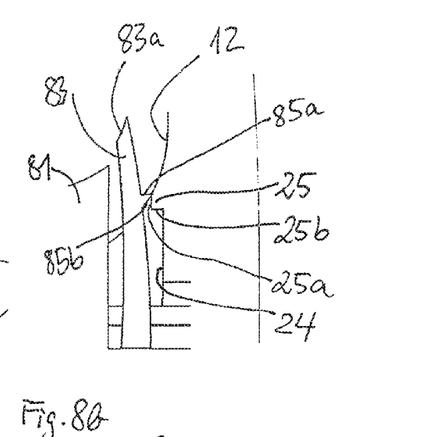
Figure 9A:
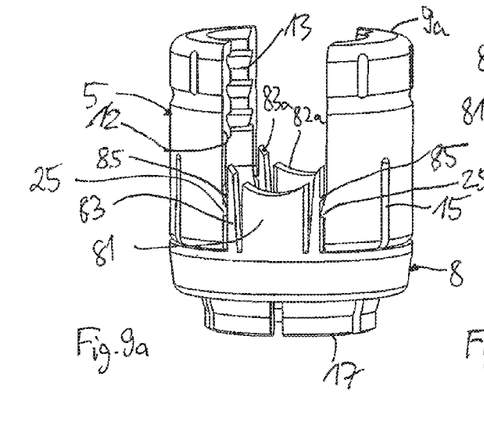
FIG. 9a shows a perspective view of the receiving part with locking ring of FIG. 1, the locking ring mounted in the first position, which allows introduction of a head of a bone anchoring element.
Figure 9B:
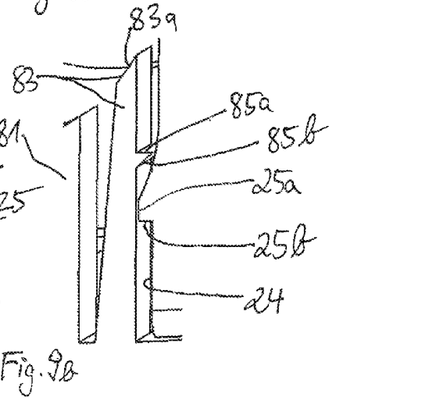

Then, as shown in FIGS. 8*a* and 8*b*, the upwardly extending spring portions 83 are deflected inwards towards the projection 81 manually or with an instrument, so that the horizontally extending projections 85 snap behind the noses 25 and into the U-shaped recess 12. This latter condition or position is shown in FIGS. 9*a* and 9*b*. When the horizontal projections 85 are above the noses 25, the upwardly extending spring portions 83 can expand and assume their undeflected positions again. In this position, the locking ring 8 is secured against falling off of receiving part 5, since the locking ring 8 is loosely held by the noses 25. Furthermore, the locking ring 8 is secured against rotation, since the spring portions 83 and the projections 81 extend into the U-shaped recess 12. The locking ring 8 can be shifted upwards until its upper edge 8*a* abuts against the second end 9*b* as shown in FIGS. 9*a* and 9*b*. The cylindrical inner wall portion 8*c* of the locking ring 8 is above the curved outer surface portion 16*a* of the head receiving portion 16, so that the head receiving portion 16 is not compressed. Between the cylindrical inner wall portion 8*c* of the locking ring 8 and the outer surface of the head receiving portion 16, there is a space which allows for expansion of the head receiving portion 16 for introduction of the head 3 of the bone anchoring element 1. In some embodiments, the receiving part 5 and the locking ring 8 may be pre-assembled in such a way that the locking ring is in an open position as shown in FIGS. 9*a* and 9*b*.

The assembly and operation of the bone anchoring device will now be described with reference to FIGS. 10*a* to 11*b*. After the introduction of the head 3 from the free end 17 into the internal hollow section 18 of the head receiving portion 16, the locking ring 8 is shifted downward towards the free end 17 manually or with an instrument. During this step, the inclined lower surface 85*b* of the horizontally extending projections 85 slide along curved portions of the U-shaped recess 12. Since the width of the U-shaped recess 12 gradually decreases in the curved portions, the upwardly extending spring portions 83 are deflected inwards towards the projections 81 until the horizontally extending projections 85 snap under the noses 25. The cutouts 24 provide a space for the horizontally extending projections 85, such that the upwardly extending spring portions 83 can assume their undeflected state. In the position shown in FIGS. 10*a* and 10*b*, the locking ring 8 is prevented from moving upward by the abutment of the upper horizontal surface 85*a* to the lower horizontal surface 25*b* of the nose 25, forming a stop. Since the locking ring 8 is in a position which at least partly covers the curved outer surface portion 16*a* of the head receiving portion 16, the head receiving portion 16 is no longer expandable, which prevents removal of the head 3 from the head receiving portion 16. This position of the locking ring is a pre-locking position. If the size of the locking ring 8 and the head receiving portion 16 are such that in the pre-locking position the head receiving portion 16 is slightly compressed, the bone anchoring element 1. may be held in a preliminary angular position with respect to the receiving part 5 by friction. The bone anchoring element may still be pivotable with respect to the receiving part 5 by applying a force greater than the friction force to pivot the bone anchoring element 1.

Figure 11A:
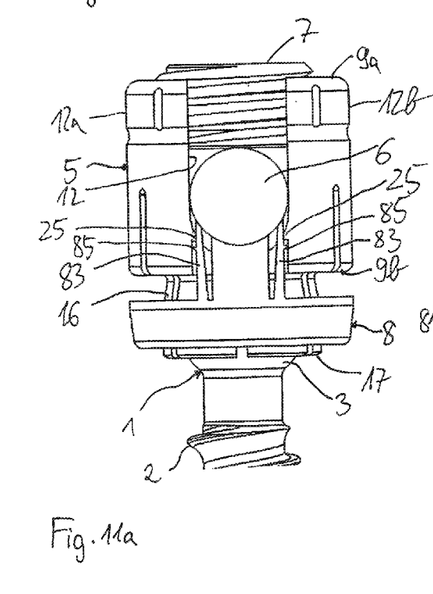
FIG. 11a shows a side view of the bone anchoring device of FIG. 1, with an inserted rod and a locking ring in a third position, in which the bone anchoring device locks the head in the receiving part.
Figure 11B:
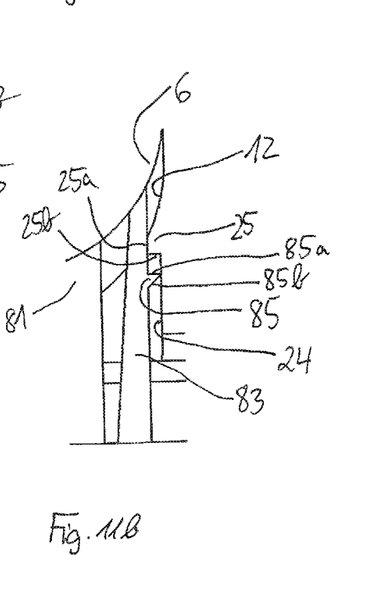

In FIGS. 11*a* and 11*b*, the locking ring 8 assumes a third position with respect to the receiving part 5, in which the locking ring 8 is shifted further downward by the rod 6, which presses on the upper surface 82 of the projection 81 and the upper portion 83*a* of the upwardly extending spring portions 83 when the inner screw 7 is tightened. This third position is a locking position. When shifting downward, the locking ring 8 exerts an increasing compression force onto the head receiving portion 16, which finally locks the head 3 at a desired angular position within the head receiving portion 16.

There are different ways of clinical use of the bone anchoring device according to embodiments of the invention. If the locking ring 8 and the receiving part 5 are pre-assembled one can select a suitable bone anchoring element 1 and connect it to the receiving part 5 when the locking ring 8 is in the first position shown in FIGS. 9*a* and 9*b*. This can be done at any time before or during surgery. The bone anchoring device can in this case be provided as a modular system, in which the surgeon can select a suitable bone anchoring element 1 to be connected to the receiving part 5.

Figures 10A, 10B:
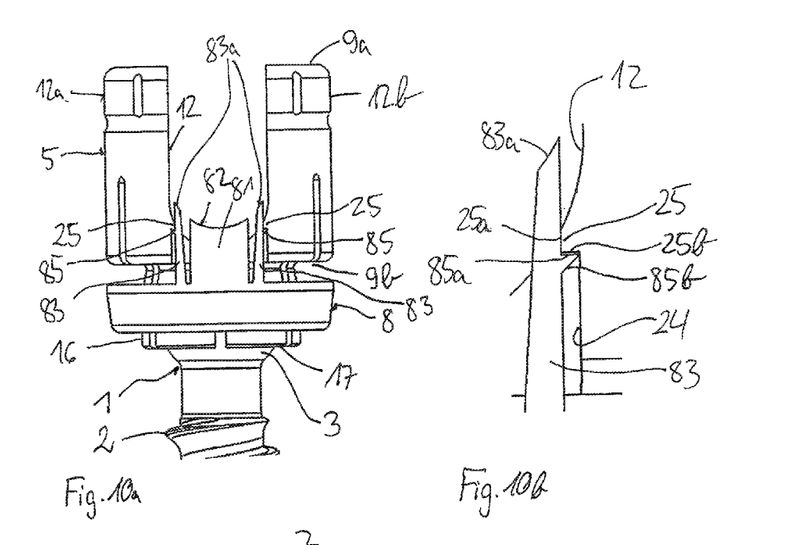

Alternatively, the receiving part 5, the locking ring 8, and the bone anchoring element 1 can be pre-assembled and provided in the pre-locking condition. Usually, several bone anchoring devices are to be connected to a spinal rod 6. In a first step, the bone anchoring elements 1 may be inserted into bone parts or vertebrae by engaging the recess 4 in the head 3 with a driver or tool. The free end 17 of the head receiving portion may be advanced to abut against a bone surface. In this case, the receiving part 5 and the bone anchoring element 1 will not be disassembled, since in the pre-locking position as shown in FIGS. 10*a* and 10*b*, the head 3 is prevented from removal from the head receiving portion 16.

After inserting the bone anchoring elements 1 in bone, the receiving parts 5 may be adjusted by pivoting them with respect to the bone anchoring elements 1 to be aligned with a rod 6 to be inserted. After insertion of the rod 6, the inner screws 7 are tightened to press the rod 6 against the upper surfaces 82 and 83a of the projections 81 and the spring portions 83, respectively, which in turn moves the locking ring 8 downward to compress the head receiving portion 16 to lock the head 3 therein.

Although the bone anchoring device according to the above embodiments is shown to have two upwardly extending spring portions 83, which are arranged on either side of the projections 81, only one spring portion may be sufficient in other embodiments. Further, the spring portions and the noses are not limited to the specific shapes shown in the described embodiments. Various other shapes which fulfill the function that the locking ring 8 is held by a stop in a pre-locking position may also be employed. For example, a spring portion could be provided at or near the inner wall of the U-shaped recess 12, which engages a rigid portion provided on the locking ring 8. Also, in another embodiment, the projections 81 can be omitted and their function can be fulfilled by the upwardly extending spring portions 83.

In addition, all kinds of anchoring elements can be used and combined with the receiving part 5. These anchoring elements may include, for example, screws of different length, with different diameters, cannulated screws, screws with different thread forms, nails, etc. The head of the anchoring element and the shaft of the anchoring element can also be separate parts which are connectable to each other.

The shape of the receiving part is also not limited to the embodiments shown. For example, the slits 20 and/or 20a in the rod receiving portion 9 can be omitted. Further, the receiving part can have an asymmetric or inclined end portion for allowing a greater pivot angle of the bone anchoring element 1 to one side.

In another embodiment, the channel for the rod can be closed on the first end of the rod receiving portion. In such embodiments, for the closure element, outer nuts or various other closure elements can be used, While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof

What is claimed is:

1. A bone anchoring device comprising:
   a bone anchoring element comprising a shaft for anchoring in a bone and a head;
   a receiving part for coupling a rod to the bone anchoring element, the receiving part comprising:
      a rod receiving portion having a first end, a second end, and a channel with a bottom for receiving a rod, and
      a head receiving portion adjacent to the second end for accommodating the head, the head receiving portion having a free end and being flexible to allow introduction and clamping of the head; and
   a locking ring configured to be positioned around the head receiving portion, the locking ring comprising at least one projection and a first engagement portion;
   wherein the rod receiving portion has at least one cutout at an end of the channel extending from the bottom of the channel to the second end of the rod receiving portion, wherein an inner wall of the cutout has a second engagement portion;
   wherein when the head is in the head receiving portion and the locking ring is around the head receiving portion in a position in which the head is pivotable with respect to the receiving part, the at least one projection is configured to extend through the at least one cutout and into the channel; and
   wherein when the head is in the head receiving portion and the locking ring is in a first position, the head is pivotable in the head receiving portion but the locking ring prevents removal of the head from the head receiving portion by restricting expansion of the head receiving portion, and the first engagement portion engages the second engagement portion at the inner wall of the cutout to prevent movement of the locking ring towards the first end of the rod receiving portion while permitting movement of the locking ring towards the free end of the head receiving portion to a second position where the engagement portions are out of engagement and the locking ring compresses the head receiving portion to lock the head in the receiving part.

2. The bone anchoring device of claim 1, wherein the first engagement portion is configured to flexibly move with respect to the second engagement portion.

3. The bone anchoring device of claim 2, wherein the first engagement portion is provided on a spring portion that is configured to extend into the channel.

4. The bone anchoring device of claim 3, wherein the projection and the spring portion are separated from one another, and wherein the spring portion is configured to flexibly move towards the projection.

5. The bone anchoring device of claim 3, wherein a free end of the spring portion comprises a support for the rod.

6. The bone anchoring device of claim 1, wherein the locking ring can assume an open position around the head receiving portion that is different from the first position, in which the head receiving portion is not compressed and is expandable to allow introduction of the head.

7. The bone anchoring device of claim 6, wherein when the locking ring is in the open position, the first engagement portion extends into the channel.

8. The bone anchoring device of claim 1, further comprising a closure element for securing the rod in the channel.

9. The bone anchoring device of claim 8, wherein the closure element comprises a set screw.

10. The bone anchoring device of claim 1, wherein the locking ring is movable towards the free end of the head receiving portion to the first position, and wherein when the locking ring is in the first position, the first engagement portion has a surface that abuts against a surface of the second engagement portion that prevents the locking ring from moving from the first position back towards the first end of the rod receiving portion.

11. The bone anchoring device of claim 1, wherein cutouts are provided at either end of the channel and two projections are provided on the locking ring that are configured to extend through the cutouts, respectively, and into the channel, and wherein at least one engagement portion corresponding to each projection is provided.

12. The bone anchoring device of claim 1, wherein in the second position where the head is locked in the receiving part, the first engagement portion extends into the cutout and is not in contact with the second engagement portion.

13. The bone anchoring device of claim 1, wherein when the locking ring is around the head receiving portion, the first and second engagement portions extend substantially in a circumferential direction of the locking ring.

14. The bone anchoring device of claim 1, wherein a diameter of the head receiving portion adjacent to the second end of the rod receiving portion is smaller than a diameter of the second end of the rod receiving portion.

15. The bone anchoring device of claim 1, wherein an outer diameter of the locking ring is smaller than or equal to an outer diameter of the rod receiving portion.

16. The bone anchoring device of claim 1, wherein the head receiving portion has at least one slit being open to the free end.

17. The bone anchoring device of claim 1, wherein the rod receiving portion has at least one slit.

18. The bone anchoring device of claim 1, wherein the head is spherical segment-shaped and the head receiving portion has an inner surface with a corresponding spherical portion to allow for pivotal movement of the head when the head is inserted in the head receiving portion.

19. The bone anchoring device of claim 1, wherein the locking ring is movable to the first position from a position where the first engagement portion on the locking ring is farther away from the free end of the head receiving portion than the second engagement portion is to the free end of the head receiving portion.

20. A method of coupling a rod to a bone or vertebrae via a bone anchoring device, the bone anchoring device comprising: a bone anchoring element comprising a shaft for anchoring in a bone and a head, a receiving part comprising a rod receiving portion having a first end, a second end, a channel with a bottom for receiving a rod, at least one cutout at an end of the channel extending from the bottom of the channel to the second end of the rod receiving portion, wherein an inner wall of the cutout has a second engagement portion, the receiving part further comprising a head receiving portion adjacent to the second end of the rod receiving portion for accommodating the head of the bone anchoring element, the head receiving portion having a free end and being flexible to allow introduction and clamping of the head, the bone anchoring device further comprising a locking ring configured to be positioned around the head receiving portion, the locking ring comprising at least one projection and a first engagement portion, the method comprising:
   introducing the head of the bone anchoring element through the free end into the head receiving portion when the locking ring is around the head receiving portion in a first position in which the at least one projection extends through the at least one cutout and into the channel;
   moving the locking ring from the first position to a second position where the head is pivotable in the head receiving portion but the locking ring prevents removal of the head from the head receiving portion by restricting expansion of the head receiving portion, and where the first engagement portion engages the second engagement portion at the inner wall of the cutout to permit movement of the locking ring towards the free end of the head receiving portion while preventing movement of the locking ring back towards the first position;
   inserting the bone anchoring element into a bone or vertebrae;
   pivoting the receiving part relative to the bone anchoring element;
   inserting a rod into the channel of the rod receiving portion; and
   advancing a closure element in the channel to push the rod against the at least one projection of the locking ring to move the locking ring from the second position to a locking position where the engagement portions are out of engagement and the head receiving portion is compressed to lock the head in the head receiving portion and to lock the respective positions of the rod and the bone anchoring element relative to the receiving part.

21. The method of claim 20, wherein the bone anchoring element is inserted into the bone or vertebrae prior to introducing the head of the bone anchoring element into the head receiving portion.

22. The method of claim 20, wherein the bone anchoring element is inserted into the bone or vertebrae after introducing the head of the bone anchoring element into the head receiving portion.

* * * * *